(12) United States Patent
Baudin

(10) Patent No.: US 9,555,953 B2
(45) Date of Patent: Jan. 31, 2017

(54) SPRAY HEAD AND CONTAINER THUS EQUIPPED, METHOD AND USE

(75) Inventor: Gilles Baudin, Montigny les Cormeilles (FR)

(73) Assignee: L'OREAL, Paris (FR)

( * ) Notice: Subject to any disclaimer, the term of this patent is extended or adjusted under 35 U.S.C. 154(b) by 19 days.

(21) Appl. No.: 14/355,813

(22) PCT Filed: Aug. 31, 2012

(86) PCT No.: PCT/IB2012/054495
§ 371 (c)(1),
(2), (4) Date: Jul. 25, 2014

(87) PCT Pub. No.: WO2013/064918
PCT Pub. Date: May 10, 2013

(65) Prior Publication Data
US 2015/0122833 A1    May 7, 2015

Related U.S. Application Data

(60) Provisional application No. 61/566,732, filed on Dec. 5, 2011.

(30) Foreign Application Priority Data

Nov. 3, 2011  (FR) ...................................... 11 59968

(51) Int. Cl.
*B05B 1/14*  (2006.01)
*B65D 83/30*  (2006.01)
(Continued)

(52) U.S. Cl.
CPC .............. *B65D 83/30* (2013.01); *A45D 34/00* (2013.01); *A61K 8/046* (2013.01); *A61Q 5/06* (2013.01);
(Continued)

(58) Field of Classification Search
CPC .................... B05B 9/04–9/0894; B05B 1/042; B05B 3/1057; B05B 12/04; B05B 12/002; B05B 1/14; B05B 1/02–1/06; A45D 34/00; A45D 2200/057; B65D 83/30; B65D 83/34; B65D 83/44; B65D 83/28; B65D 83/206; A61Q 5/06; A61Q 15/00; A61K 8/046
(Continued)

(56) References Cited

U.S. PATENT DOCUMENTS 3,504,862 A * 4/1970 Lowry ...................... B05B 1/14
  222/565
3,724,763 A * 4/1973 Braun ................... B05B 1/3426
  239/490
(Continued)

FOREIGN PATENT DOCUMENTS

FR         1 600 138         8/1970
WO    WO 2013/064918 A1    5/2013

OTHER PUBLICATIONS

The International Search Report for corresponding International Application No. PCT/IB2012/054495, dated Jan. 3, 2013.
(Continued)

*Primary Examiner* — Darren W Gorman
*Assistant Examiner* — Juan C Barrera
(74) *Attorney, Agent, or Firm* — Jones Robb, PLLC

(57) ABSTRACT

Head for spraying a product in a spraying direction, for example a cosmetic product, in particular a deodorant, this spray head comprising: a body, comprising: a channel for conveying the product, a housing in which the conveying channel emerges, the spray head also comprising: a spray nozzle mounted on the housing, this nozzle comprising at least two, better still three, spray orifices, respective feed channels being formed between the nozzle and the body, these channels connecting the conveying channel to the said (Continued)

Figure 2:
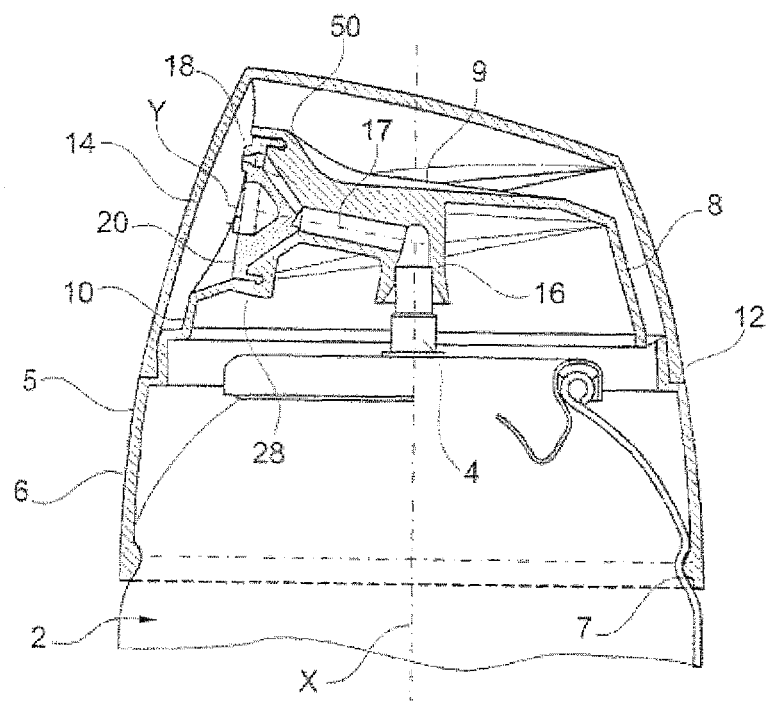

corresponding spray orifices, and being obliquely inclined relative to the spraying direction.

24 Claims, 3 Drawing Sheets

(51) Int. Cl.
| | |
|---|---|
| *A45D 34/00* | (2006.01) |
| *B65D 83/34* | (2006.01) |
| *B65D 83/20* | (2006.01) |
| *B65D 83/28* | (2006.01) |
| *A61Q 5/06* | (2006.01) |
| *A61Q 15/00* | (2006.01) |
| *A61K 8/04* | (2006.01) |
| *B65D 83/44* | (2006.01) |

(52) U.S. Cl.
CPC .............. *A61Q 15/00* (2013.01); *B05B 1/14* (2013.01); *B65D 83/206* (2013.01); *B65D 83/28* (2013.01); *B65D 83/34* (2013.01); *B65D 83/44* (2013.01); *A45D 2200/057* (2013.01)

(58) Field of Classification Search
USPC ............... 239/337, 338, 375, 548–568, 596; 222/402.1, 402.13, 330, 485, 401
See application file for complete search history.

(56) References Cited

U.S. PATENT DOCUMENTS

| | | | | |
|---|---|---|---|---|
| 3,767,125 | A * | 10/1973 | Gehres | B65D 83/20 239/552 |
| 5,730,332 | A * | 3/1998 | Zimmerhackel | B05B 7/0068 222/148 |
| 6,158,674 | A * | 12/2000 | Humphreys | B05B 1/14 222/321.6 |
| 6,415,993 | B1 * | 7/2002 | Forbert | B01F 5/0403 239/434 |
| 6,971,557 | B2 * | 12/2005 | Mather | B65D 83/206 222/182 |
| 7,984,832 | B2 * | 7/2011 | Pivonka | A45D 34/04 222/205 |
| 2006/0278732 | A1 | 12/2006 | Daugherty | |

OTHER PUBLICATIONS

The Written Opinion of the International Searching Authority for corresponding International Application No. PCT/IB2012/054495, dated Jan. 3, 2013.

The French Preliminary Search Report and Written Opinion for corresponding French Application No. 1159968, dated Jun. 25, 2012.

English language abstract of FR 1 600138, original document dated Aug. 28, 1970.

* cited by examiner

Total diameter of 16 cm

SPRAY HEAD AND CONTAINER THUS EQUIPPED, METHOD AND USE

This is a national stage application of PCT/IB2012/054495, filed internationally on Aug. 31, 2012, which claims priority to U.S. Provisional Application No. 61/566,732, filed on Dec. 5, 2011, as well as French Patent Application No. FR 1159968, filed on Nov. 3 2011, the entire contents each of which is incorporated herein by reference.

The present invention relates to devices for dispensing a fluid product and more particularly but not exclusively to heads for spraying a cosmetic product, such as, for example, a deodorant (including antiperspirants), or a hair product, for example a product for shaping the hair.

Patent FR 1 600 138 discloses a dispensing head comprising a push button, the body of which is traversed by a conveying channel and terminates in a housing receiving a nozzle having three spray orifices.

The housing exhibits a flat bottom and the nozzle comprises radial grooves which make it possible to define, after assembling on the body of the push button, channels connecting the conveying channel to the dispensing orifices. These channels are oriented perpendicularly to the spraying direction and to the longitudinal axis of the conveying channel.

One disadvantage of this head is that of creating a relatively high drop in pressure due to the route of the product, which comprises multiple changes in direction and right-angle returns. Furthermore, this route increases the risks of blockage, in the case of the use of a product which, on drying, produces a dry residue.

There exists a need to increase the speed of application of a product by spraying without, however, increasing the risks of blockage related to the drying of the sprayed product.

There exists a need to have available a spray head which generates a relatively narrow spray cone and/or around the axis of which the concentration of product is as high as possible.

There also exists a need to have available a spray head which makes it possible to project the sprayed product with as high a force as possible in order to enhance the feeling of effectiveness.

The invention is targeted at meeting the abovementioned needs in all or part and also at further improving the known spray heads while making possible the use of manufacturing techniques having a cost compatible with large-scale dissemination.

A subject-matter of the invention, according to a first of its aspects, is a head for spraying a product in a spraying direction, for example a cosmetic product, in particular a deodorant, this spray head comprising:
 a body, comprising:
  a channel for conveying the product,
  a housing in which the conveying channel emerges,
 the spray head also comprising:
  a spray nozzle mounted on the housing,
 this nozzle comprising at least two, better still three, spray orifices,
 respective feed channels being formed between the nozzle and the body, these channels connecting the conveying channel to the said corresponding spray orifices, and being obliquely inclined relative to the spraying direction.

The term "oblique" should be understood as meaning neither parallel nor perpendicular.

The invention makes it possible to have available a spray head offering a relatively high product flow rate as the inclination of the feed channels, without a right-angle return, does not greatly slow down the speed of the flow, and furthermore reduces the risk of blockage by local accumulation of the product when spraying is halted.

It is easy to mould the nozzle since the feed channels are formed during the fitting of the nozzle to the housing of the body of the head and do not require the use of a mould with slides. Furthermore, it is easy to give, by moulding, these channels the desired orientation suited to reducing the risks of accumulation of product.

The nozzle can be fixed in its housing without prior angular location of its orientation around its axis, the orientation of the nozzle in the housing thus being random. This facilitates the fitting operation.

The channels extend along respective longitudinal axes which are preferably obliquely inclined with respect to the spraying direction by an angle of between 30° and 60°, more preferably of the order of 45°. Preferably, the angle is the same for all the feed channels.

Preferably, the nozzle comprises recesses which partially define the said channels, these recesses being, for example, of semi-circular transverse cross-section. This makes it possible to produce the housing with a smooth conical surface, for example. In an alternative recesses are formed in the housing, in order to at least partially define the feed channels, and the rear face of the nozzle is smooth. However, in this case, locating the orientation of the nozzle relative to the housing is necessary.

The nozzle can comprise only three spray orifices, which are then advantageously positioned at 120° with respect to one another, around the axis of the nozzle.

The spray orifices can have axes which are parallel to one another and parallel to the spraying direction, which preferably coincides with the axis of the nozzle. The axes of the spray orifices are offset with respect to the axis of the nozzle and to the axis of the conveying channel.

The nozzle can be fixed in various ways in the housing; preferably, the nozzle is snapped into the latter. To this end, the nozzle can comprise a peripheral fitting skirt provided with one or more raised parts used for snapping onto the body of the spray head. This or these raised parts can be present on the exterior surface of the fitting skirt, for example in the form of an annular notch.

The nozzle exhibits a front face on which the spray orifices emerge. This front face is preferably a face which is fully visible when the nozzle is fitted to the dispensing head, which makes it possible, by using, to produce the nozzle, a material having a different colour from that of the body, to contribute to improving the attractiveness of the spray head and to facilitating the locating of the nozzle by the user.

The spray orifices can emerge on respective bosses projecting from this front face of the nozzle or, in an alternative form, emerge on a flat front face or set back from the front face.

The front face can also exhibit a central cutout, around which the spray orifices are positioned. This central cutout can exhibit a conical bottom. The presence of the central cutout can facilitate the production of recesses obliquely inclined over the nozzle, by making it possible to reduce the thickness of material along these recesses and to have, for example, a substantially constant thickness favourable with regard to the manufacturing costs.

The spray orifices can terminate in a narrowing of their cross-section. For example, the spray orifices each comprise a cylindrical section which is connected to a corresponding feed channel, a conical section for reducing the cross-section and a final cylindrical section having a small diameter, from which the fluid is ejected. It is thus possible to have a relatively large cross-section until close to the outlet and to conserve the kinetic energy of the flow, which makes it possible to generate a powerful spray having a high flow rate, which allows the possibility of choosing a low-pressure propellant without loss of diffusion quality.

The body of the spray head is advantageously one-piece and can be produced with at least one raised part intended to fix it to a container, for example a pressurised aerosol can.

The conveying channel can be produced within a push button, which is preferably connected via a flexible portion to a fitting hoop on the container.

The dispensing head can be produced so as to make possible the fitting on the latter of a protective cap, which is, for example, fixed to the head by snapping.

The container to which the spray head according to the invention is fitted can contain a deodorant or any other product to be sprayed, for example another cosmetic product, a care product or a product intended for a household application.

The product can be a cosmetic product, for example chosen from body hygiene products, deodorant or antiperspirant products, styling products or colouring products.

The conveying channel can extend along an axis which is not perpendicular to the longitudinal axis of the container, when the spray head is fitted to the latter, in order in particular to promote the flow of the product after spraying and to reduce even further the risk of blockage of the spray head.

A further subject-matter of the invention is a packaging and dispensing device comprising:
 a dispensing head according to the invention,
 a container equipped with the dispensing head.

A further subject-matter of the invention is a method for the cosmetic treatment of human keratinous substances, preferably the skin, comprising a stage of spraying at least one cosmetic product over the said keratinous substances, the spraying being carried out using a spray head as defined above.

When the product is sprayed over a target 15 cm away from the spray head and perpendicular to the axis of spraying:
 at least 50%, preferably at least 60%, preferably at least 65%, indeed even at least 70%, of the weight of product sprayed can reach a disc of the target centered on the axis of spraying and with a radius of 2 cm, and/or
 at least 50%, preferably at least 60%, preferably at least 65%, preferably at least 70%, preferably at least 75%, preferably at least 80%, preferably at least 85%, of the weight of product sprayed can reach a disc of the target centered on the axis of spraying and with a radius of 4 cm, and/or
 at least 50%, preferably at least 60%, preferably at least 65%, preferably at least 70%, preferably at least 75%, preferably at least 80%, preferably at least 85%, preferably at least 90%, of the weight of product sprayed can reach a disc of the target centered on the axis of spraying and with a radius of 6 cm, and/or
 at least 50%, preferably at least 60%, preferably at least 65%, preferably at least 70%, preferably at least 75%, preferably at least 80%, preferably at least 85%, preferably at least 90%, preferably at least 95%, of the weight of product sprayed can reach a disc of the target centered on the axis of spraying and with a radius of 8 cm.

This high convergence of the sprayed jet advantageously makes it possible to increase the effectiveness thereof.

It also increases its impact on the treated area, which improves the feeling of the user. Finally, it improves the accuracy.

The cosmetic product can be sprayed over the skin or, in an alternative form, over the keratinous fibres, preferably the hair.

A further subject-matter of the invention is the use of a spray head as described above for the spraying of a cosmetic product over keratinous substances, in order to improve the accuracy of the spraying of the cosmetic product and/or the concentration of the cosmetic product close to the axis of spraying. Preferably, the spraying is such that, when the product is projected onto a target 15 cm away from the spray head and perpendicular to the axis of spraying:
 at least 50%, preferably at least 60%, preferably at least 65%, indeed even at least 70%, of the weight of product sprayed reaches a disc of the target centered on the axis of spraying and with a radius of 2 cm, and/or
 at least 50%, preferably at least 60%, preferably at least 65%, preferably at least 70%, preferably at least 75%, preferably at least 80%, preferably at least 85%, of the weight of product sprayed reaches a disc of the target centered on the axis of spraying and with a radius of 4 cm, and/or
 at least 50%, preferably at least 60%, preferably at least 65%, preferably at least 70%, preferably at least 75%, preferably at least 80%, preferably at least 85%, preferably at least 90%, of the weight of product sprayed reaches a disc of the target centered on the axis of spraying and with a radius of 6 cm, and/or
 at least 50%, preferably at least 60%, preferably at least 65%, preferably at least 70%, preferably at least 75%, preferably at least 80%, preferably at least 85%, preferably at least 90%, preferably at least 95%, of the weight of product sprayed reaches a disc of the target centered on the axis of spraying and with a radius of 8 cm.

A further subject-matter of the invention is a cosmetic kit, in particular for the use of a method as defined above, comprising, within one and the same packaging:
 a spray head as defined above, and
 a cosmetic product chosen from body hygiene products, deodorant or antiperspirant products, styling products or colouring products.

The kit can additionally comprise a container intended to contain the cosmetic product and on which the dispensing head is intended to be positioned and fixed.

The cosmetic product may or may not be present in the container within the kits according to the invention.

Figures 1, 3:
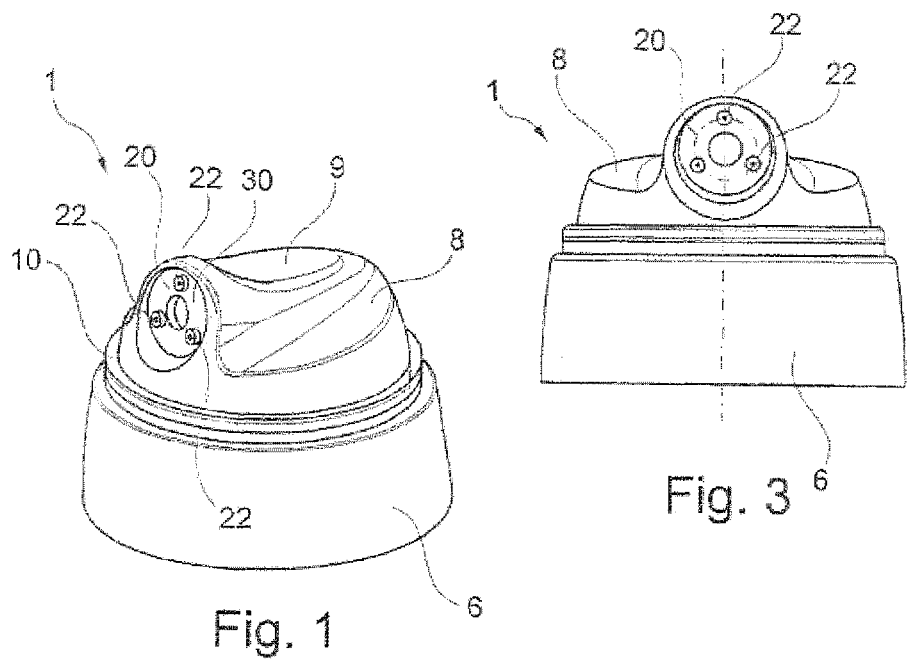
Figure 5:
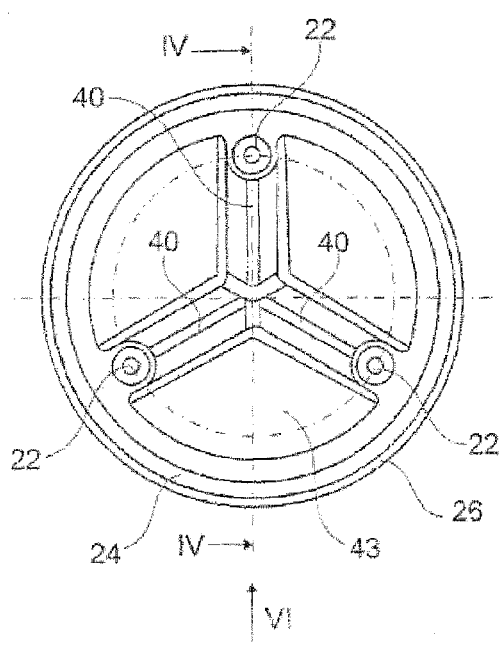
Figure 4:
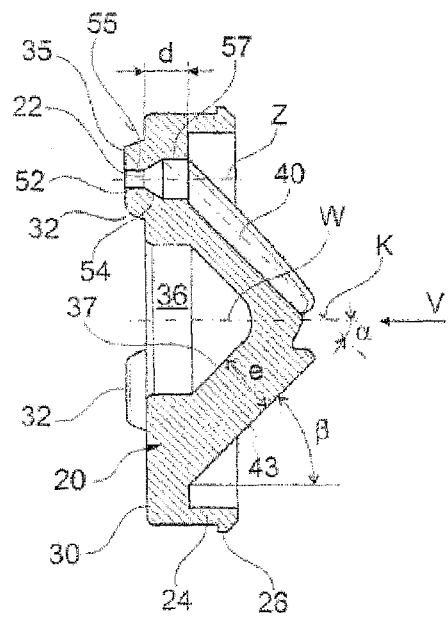
Figure 6:
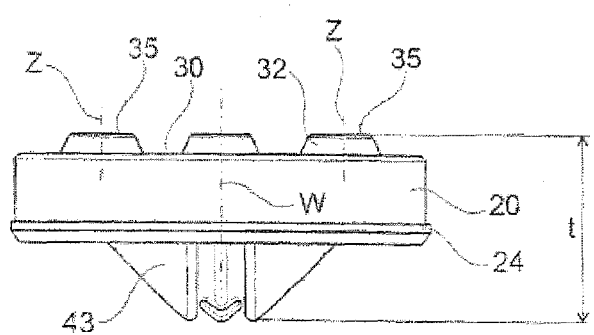
Figure 7:
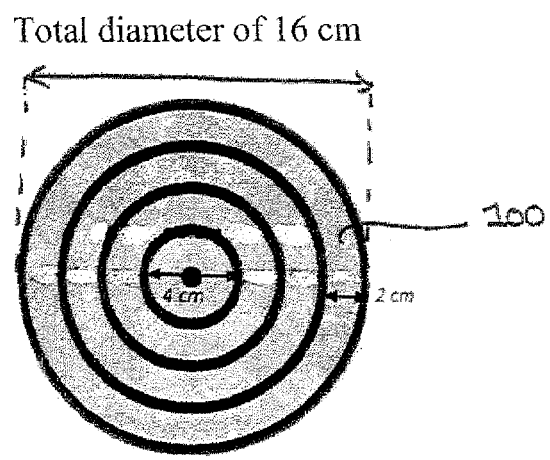
Figure 8:
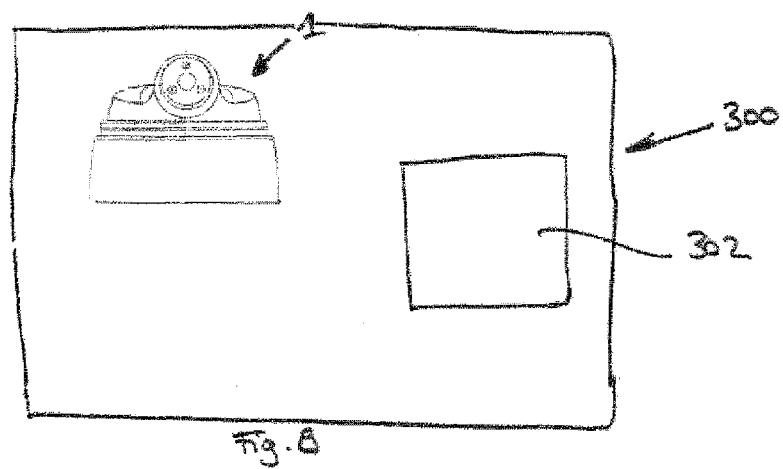

The invention may be better understood on reading the following detailed description of a non-limiting implementational example thereof and on examining the appended drawings, in which:

FIG. 1 represents in perspective, in isolation, the dispensing head according to the invention, protective cap removed, FIG. 2 represents the dispensing head, fitted to a container with the protective cap in place, in partial and diagrammatic longitudinal cross-section, FIG. 3 is a front view of the dispensing head, represented in isolation, FIG. 4 represents, in isolation, in axial cross-section, the spray nozzle, FIG. 5 is a rear view along V of FIG. 4, FIG. 6 is a side view along VI of FIG. 5, FIG. 7 diagrammatically represents a target used to evaluate the ability of a spray head according to the invention to provide concentrated spraying of an active ingredient, and FIG. 8 diagrammatically represents a cosmetic kit according to the invention.

The spray head 1 represented in the figures is intended to equip a container 2, for example an aerosol can, comprising a product which is dispensed under the pressure of a propellant gas. It is, for example, a deodorant.

The dispensing head 1 can also be fitted, in an alternative form not illustrated, on a bottle equipped with a pump.

In the example of FIGS. 1 to 3, the container 2 is equipped with a valve for release by pushing in a hollow control rod 4 along the longitudinal axis X of the container. In an alternative form, the valve is for release by tipping.

The dispensing head 1 comprises means for fitting to the container 2 which comprise, in the example illustrated, a hoop 6, also known as fitting skirt, intended to be snapped over an annular recess 7 produced on the container 2, in a way known per se.

In alternative forms not illustrated, the dispensing head 1 is fitted otherwise to the container containing the product to be sprayed, for example being screwed, welded or adhesively bonded to the container. The container can also be produced at least partially by moulding with the body of the dispensing head.

In the example illustrated, the body 5 of the dispensing head 1 comprises a push button 8 which defines a surface 9 on which the user can press in order to dispense the product. The push button 8 is connected to the hoop 6 by a flexible portion 10 which, in the example under consideration, is situated on the side of the dispensing head from which the product is sprayed.

The hoop 6 defines, in the upper part, a shoulder 12, which makes it possible to fit a protective cap 14, which is advantageously made of a transparent thermoplastic material.

The push button 8 is produced with a joining piece 16 interlocked over the valve rod 4, this joining piece 16 being in communication with a conveying channel 17, the longitudinal axis Y of which is non-perpendicular to the longitudinal axis X of the container, being inclined upwards, when the container 2 is vertical and the dispensing head 1 is fixed above.

The hoop 6, the flexible portion 10 and the push button 8 are moulded from a single part in a thermoplastic material, for example polypropylene (PP).

The conveying channel 17 emerges in the bottom of a housing 18, which receives a spray nozzle 20.

The nozzle 20 exhibits several spray orifices 22, numbering three in the case in point, the axes Z of which are parallel to the spraying direction, which coincides with the longitudinal axis Y of the conveying channel 17.

The nozzle 20 comprises, at its periphery, a tubular fitting skirt 24 which is used to fix the nozzle 20 to the body 5. This skirt 24, with an axis W, exhibits, on its exterior surface, a raised part, for example in the form of an annular notch, as illustrated in FIG. 4, which is designed in order to be snapped into a recess 28 of corresponding shape produced in the push button 8.

The orifices 22 emerge on a front face 30 of the nozzle 20, which is visible after the nozzle has been fitted to the push button 8.

The nozzle 20 is produced by moulding thermoplastic material, for example made of PP or POM.

The front face 30 exhibits three bosses 32 which project therefrom, the orifices 22 emerging at the top 35 of these bosses. These bosses 32 exhibit, for example, as illustrated, a top 35 which is substantially flat and perpendicular to the axis W. In the example illustrated, the nozzle 20 is devoid of channels which produce swirling, the orifices 22 being directional.

The nozzle 20 comprises a central indentation 36, which emerges on the front face 30 and which has a bottom 37 which is substantially conical.

The nozzle 20 comprises, on its rear face 43, which exhibits a general dome shape, three recesses 40 each extending longitudinally along an axis K which forms, with the axis W of the nozzle 20, an angle α preferably of approximately 45°.

Apart from the recesses 40, the wall of the nozzle 20 extending between the rear face 43 and the central indentation 36 exhibits a substantially constant thickness e, as may be seen in FIG. 4. The slope β of the rear face 43, with respect to the axis W, is, for example, equal to the angle α, as illustrated.

The recesses 40 define, with the bottom of the housing 18 of the push button 8 which receives them, feed channels 50 which connect the conveying channel 17 to the spray orifices 22.

The bottom of the housing 18 is produced with a conical shape generated by rotation around the axis Y of the conveying channel 17.

These terminate, as may be seen in FIG. 4, in a narrowing 52 of their interior cross-section. More specifically, each feed channel 50 is connected to a cylindrical section generated by rotation 57, having the axis Z. A conical section 54 converging towards the outlet connects the section 57 to another cylindrical section 55 generated by rotation, having a smaller diameter, which emerges on the top 35 of the bosses 32.

The diameter of the cylindrical section 55 is, for example, 0.25 mm and that of the cylindrical section 57 is 0.6 mm. The axial dimension d of the conical section 54 and of the cylindrical section 57, considered together, is, for example, between 1 and 1.5 mm, for example being 1.3 mm, and the axial dimension of the cylindrical section 55 is, for example, between 0.4 and 0.8 mm, for example being 0.6 mm.

The external diameter of the nozzle 20 is, for example, less than or equal to 15 mm. The spray orifices 22 can be relatively close, which makes possible the formation at a short distance, for example less than 10 cm from the spray head 1, of a homogeneous spray.

The overall axial dimension t of the nozzle 20 is, for example, between 4 and 6 mm, for example being 5.7 mm.

The fitting of the nozzle 20 can be carried out without prior angular location, before it is snapped into the housing 18. The angular orientation of the nozzle 20 relative to the axis Y is thus random, from one dispensing head to the following, during the manufacturing process.

The quality of the spray is thus independent of the angular orientation of the nozzle during the fitting thereof to the body of the dispensing head.

In order to use the dispensing head 1, the user presses on the push button 8, which actuates the valve rod 4 and brings about the arrival of product under pressure in the conveying channel 17. The product moving through the conveying channel 17 is distributed in the three feed channels 40 and is directed towards the spray orifices 22, which provide for the dispensing thereof in the form of jets which meet at a nonzero distance from the nozzle.

The invention is not limited to the implementational example which has just been described. In particular, the nozzle 20 can be produced with more than three spray orifices.

Furthermore, the nozzle can be oriented with an angle with respect to the head, it being possible for the channels 40 to be formed in part in the nozzle on the rear face 43 and in part in the sheet metal in the bottom of the housing 18.

A cosmetic kit 300 according to the invention, comprising a spray head 1 according to the invention and a cosmetic product 302, for example a deodorant product, has been represented in FIG. 8.

In an alternative form which is not illustrated, the kit additionally comprises a container on which the head is intended to be positioned and fixed, the container being intended to contain the cosmetic product.

EXAMPLE

The test described in detail below shows the ability of the spray heads according to the invention to concentrate an active ingredient over a target area.

For this test, use was made of a target 100 with a diameter of 16 cm (see FIG. 7) composed of a central disc with a diameter of 4 cm and of three concentric rings, each with a width of 2 cm, encircling the central disc.

An anhydrous antiperspirant Minéral GARNIER pierre d'alun hypoallergénique, sold by L'Oréal, was sprayed in the direction of the centre of this target, for 5 seconds and at a distance of 15 cm.

After spraying, the four parts of the target are separated and weighed individually.

The weighings require a balance accurate to within a 100th.

The results are combined in the table given below.

|  | Overall weight Cumulative weight | Central disc, r = 2 cm | Ring 1, r = 4 cm | Ring 2, r = 6 cm | Ring 3, r = 8 cm |
|---|---|---|---|---|---|
| Spray head according to the invention | 0.56 g 0.53 g | 0.39 g | 0.09 g | 0.03 g | 0.02 g |
| Minéral GARNIER single-nozzle | 0.58 g 0.44 g | 0.21 g | 0.14 g | 0.05 g | 0.04 g |

The spray head according to the invention concentrates the sprayed product virtually two times more than the Minéral GARNIER single-nozzle in the central area of the target.

This test clearly demonstrates that the spray head according to the invention generates a significantly more centered spray (less divergent from the centre of the target, narrower spray cone). This is because:
- 70% of the product arrives on the central disc, whereas only 36% arrives thereon with a conventional spray head,
- 95% of the flow is found on the target, against only 75% with a conventional nozzle.

This concentrating of the active ingredient in the area of interest advantageously makes it possible to increase its effectiveness.

For example, for styling sprays, this concentrating favours the firm holding and the local shaping of the hair.

The invention is suitable for the dispensing of products other than cosmetics, for example an oven cleaner or an insecticide.

The expression "comprising a" should be understood as being synonymous with "comprising at least one".

The invention claimed is:

1. A head for spraying a product in a spraying direction, the spray head comprising:
   a body comprising:
     a channel for conveying the product, and
     a housing in which the conveying channel emerges; and
   a spray nozzle mounted on the housing, the spray nozzle comprising at least two spray orifices, the spray orifices being defined within the spray nozzle itself,
   wherein respective feed channels are formed between the spray nozzle and the body, the feed channels connecting the conveying channel to the corresponding spray orifices, and being obliquely inclined relative to the spraying direction, and
   wherein the spray orifices are positioned at 120° with respect to one another, around an axis of the spray nozzle.

2. The spray head according to claim 1, the spray nozzle being deprived of a central channel.

3. The spray head according to claim 2, wherein the feed channels extend along respective longitudinal axes which are obliquely inclined with respect to the spraying direction by an angle of between 30° and 60°.

4. The spray head according to claim 1, wherein an angle of a longitudinal axes of the feed channels relative to the spraying direction is the same for each of the feed channels.

5. The spray head according to claim 1, wherein the nozzle comprises recesses which partially define the feed channels.

6. The spray head according to claim 1, wherein the spray orifices have axes which are parallel to one another and are parallel to the spraying direction, which coincides with an axis of the spray nozzle.

7. The spray head according to claim 1, wherein the spray nozzle comprises a peripheral fitting skirt provided with one or more raised parts used for snapping onto the body of the spray head.

8. The spray head according to claim 1, wherein the spray nozzle exhibits a front face on which the spray orifices emerge, the front face being a face which is fully visible when the spray nozzle is fitted to the body of the dispensing head.

9. The spray head according to claim 8, wherein the front face exhibits a central cutout, around which the spray orifices are positioned.

10. The spray head according to claim 9, wherein the central cutout exhibits a conical bottom.

11. The spray head according to claim 1, wherein the spray orifices terminate in a narrowing of their section.

12. The spray head as claimed in claim 1, wherein the body of the spray head is one-piece and is produced with at least one raised part intended to fix the spray head to a container.

13. The spray head according to claim 12, wherein the conveying channel is produced with a push button, which is connected via a flexible portion to a fitting hoop on the container.

14. The spray head according to claim 1, wherein the spray nozzle is fixed in the housing without prior location of its orientation around its axis.

15. A method for the cosmetic treatment of human keratinous substances, comprising a stage of spraying at least one cosmetic product over the keratinous substances, the spraying being carried out using a spray head as defined in claim 1.

16. The method according to claim 15, wherein the cosmetic product is chosen from body hygiene products, deodorant or antiperspirant products, styling products, or colouring products.

17. The method according to claim 16, wherein the cosmetic product is a deodorant product.

18. The method according to claim 15, wherein the spray head makes it possible to obtain, when the product is sprayed over a target 15 cm away from the spray head and perpendicular to an axis of spraying:
   at least 50% of a weight of product sprayed which reaches a disc of the target centred on the axis of spraying and with a radius of 2 cm.

19. The method according to claim 15, wherein the product is sprayed over the skin.

20. The method according to claim 15, the product being sprayed over the keratinous fibres, preferably the hair.

21. A use of a spray head according to claim 1 for spraying a cosmetic product over keratinous substances, in order to improve accuracy of the spraying of the cosmetic product and/or a concentration of the cosmetic product close to an axis of the spraying, the spraying being configured such that, when the product is projected onto a target 15 cm away from the spray head and perpendicular to the axis of spraying:
   at least 50% of a weight of product sprayed reaches a disc of the target centered on the axis of spraying and with a radius of 2 cm.

22. A cosmetic kit comprising, with one and the same packaging:
   a spray head according to claim 1; and
   a cosmetic product chosen from body hygiene products, deodorant or antiperspirant products, styling products, or colouring products.

23. The kit according to claim 22, further comprising a container configured to contain the cosmetic product and on which the dispensing head is configured to be positioned and fixed.

24. A head for spraying a product in a spraying direction, the spray head comprising:
   a body comprising:
      a channel for conveying the product, and
      a housing in which the conveying channel emerges; and
   a spray nozzle mounted on the housing, the spray nozzle comprising at least two spray orifices,
   wherein respective feed channels are formed between the spray nozzle and the body, the feed channels connecting the conveying channel to the corresponding spray orifices, and being obliquely inclined relative to the spraying direction, and
   wherein the spray orifices emerge on respective bosses projecting from a front face of the spray nozzle.

\* \* \* \* \*